(12) United States Patent
Liu

(10) Patent No.: US 9,724,180 B1
(45) Date of Patent: Aug. 8, 2017

(54) BRUSH HEAD FOR ELECTRIC TOOTHBRUSH

(71) Applicant: Harria Investment Group Inc., Causeway Bay (HK)

(72) Inventor: Xinlan Liu, Rowland Heights, CA (US)

(73) Assignee: Harria Investment Group Inc., Hong Kong (CN)

( * ) Notice: Subject to any disclaimer, the term of this patent is extended or adjusted under 35 U.S.C. 154(b) by 0 days.

(21) Appl. No.: 15/400,369

(22) Filed: Jan. 6, 2017

(51) Int. Cl.
*A61C 17/22* (2006.01)
*A61C 17/34* (2006.01)

(52) U.S. Cl.
CPC ........ *A61C 17/222* (2013.01); *A61C 17/3481* (2013.01)

(58) Field of Classification Search
CPC ....... A61C 17/22; A61C 17/222; A61C 17/32; A61C 17/34; A61C 17/3481
USPC .................................................. 15/22.1, 22.2
See application file for complete search history.

(56) References Cited

U.S. PATENT DOCUMENTS

| | | | |
|---|---|---|---|
| 3,369,265 A * | 2/1968 | Halberstadt | A61C 17/32 15/145 |
| D563,674 S | 3/2008 | Beedham | |
| D569,623 S | 5/2008 | Beedham | |
| D580,173 S | 11/2008 | Beedham | |
| D653,035 S | 1/2012 | Gebski | |
| D657,565 S | 4/2012 | Gebski | |
| D696,517 S | 12/2013 | Gebski | |
| 8,782,841 B2 | 7/2014 | Sale et al. | |
| D718,057 S | 11/2014 | Massee et al. | |
| 9,204,948 B2 | 12/2015 | Kloster | |
| 2005/0108838 A1* | 5/2005 | Schaefer | A61C 17/22 15/22.1 |
| 2013/0333126 A1 | 12/2013 | Miller | |
| 2015/0245895 A1* | 9/2015 | Kressner | A61C 17/225 15/22.1 |

FOREIGN PATENT DOCUMENTS

| | | | |
|---|---|---|---|
| DE | 3129435 | * | 2/1983 |
| DE | 102005041459 | * | 3/2007 |
| DE | 102006060134 | * | 6/2008 |
| DE | 102007022827 | * | 11/2008 |
| JP | 53-21650 | * | 2/1978 |
| JP | 7-116028 | * | 5/1995 |
| JP | 10-52447 | * | 2/1998 |
| WO | 99/20202 | * | 4/1999 |

(Continued)

*Primary Examiner* — Mark Spisich
(74) *Attorney, Agent, or Firm* — Fox Rothschild LLP

(57) ABSTRACT

A toothbrush head may include a brush section with bristles thereon, a stem extending from the brush section and a coupling member mountable to inside the stem. The coupling member may have a body that has an opening for receiving a drive shaft of an electric toothbrush handle into the coupling member, and a handle coupling section extending from the body and having a wall and an aperture within the wall for receiving the drive shaft. The wall has at least two longitudinal slits and a resilient wall between the two slits, where the resilient wall may engage with the drive shaft when the drive shaft is inserted into the coupling member. At least a portion of the body of the coupling member and at least a portion of the stem may each have a cone shape that corresponds to each other to achieve a coupling.

20 Claims, 7 Drawing Sheets

(56) References Cited

FOREIGN PATENT DOCUMENTS

| WO | 00/76420 | * | 12/2000 |
| WO | 2009/094820 | * | 8/2009 |
| WO | 2010/001197 | * | 1/2010 |
| WO | 2013/061219 | * | 5/2013 |
| WO | 2015/059660 | * | 4/2015 |
| WO | 2016/001831 | * | 1/2016 |

* cited by examiner

BRUSH HEAD FOR ELECTRIC TOOTHBRUSH

BACKGROUND

This disclosure relates to the field of electric toothbrushes and particularly brush heads couplable to an electric toothbrush handle.

Many types of electric toothbrushes use high speed vibrations of the motor inside the toothbrush handle to drive the brush head. In order to operate the electric toothbrush, the construction of the brush head requires that it be tightly coupled to the drive shaft of the toothbrush handle so it can withstand the high speed vibrations from operating the toothbrush. Many existing products, therefore, use metal or springs inside the brush head to facilitate a tight coupling to the drive shaft of the toothbrush handle. This can increase the cost of making the brush head. It is desirable to make a toothbrush head with no or minimal use of metal that can still withstand high speed vibrations from operating the toothbrush.

This patent document describes an apparatus that may address at least some of the issues described above and/or other issues.

SUMMARY

In one embodiment, a toothbrush head includes a brush section having bristles attached thereon, a stem extending from the brush section and a coupling member mountable to inside the stem. The stem has an opening for receiving the coupling member and one or more mounting ridges on inside wall of the opening. The coupling member may have a body having an opening configured to receive a drive shaft of an electric toothbrush handle into the coupling member. The coupling member may also have one or more mounting holes that are positioned to engage with the one or more mounting ridges of the stem to secure the coupling member to the stem in position. The coupling member may also have a handle coupling section extending from the body and having a wall and an aperture within the wall for receiving the drive shaft. The wall has at least two longitudinal slits and a resilient wall between the two slits. The resilient wall is positioned to engage with the drive shaft when the drive shaft is inserted into the coupling member. The handle coupling section may further have a flat engaging surface inside the aperture that is positioned to mate with a flat surface of the drive shaft to ensure a tight coupling. The resilient wall may also have a raised portion extending inward and positioned to touch the drive shaft so that the drive shaft is tightly coupled to the handle coupling section while received in the aperture of the handle coupling section.

In various embodiments, the toothbrush head may have additional features that allow a tight coupling between the stem and the coupling member to be able to withstand high frequency vibration from operating the toothbrush. In one embodiment, the stem may further include a ridge block. The stem may also include a longitudinal channel on the inside wall of the opening. The coupling member may further include a longitudinal ridge that is positioned to engage with the longitudinal channel of the stem. The coupling member may also have a mounting channel that is positioned to engage with the ridge block of the stem.

In one embodiment, the opening of the stem has a base platform, and the opening of the body of the coupling member also has a base platform that is positioned to be flush with the base platform of the stem. Further, the stem may have a sitting platform along the inside perimeter of the opening of the stem, and the body of the coupling member may have a base ring around the outside perimeter of the opening of the body and positioned to mate with the sitting platform of the stem.

In one embodiment, at least a portion of the body of the coupling member may be in a cone shape. A portion of the stem proximate to the opening may also have a cone shape that corresponds to the cone shape of the body of the coupling member.

DETAILED DESCRIPTION

This disclosure is not limited to the particular systems, methodologies or protocols described, as these may vary. The terminology used in this description is for the purpose of describing the particular versions or embodiments only, and is not intended to limit the scope.

Figure 1:
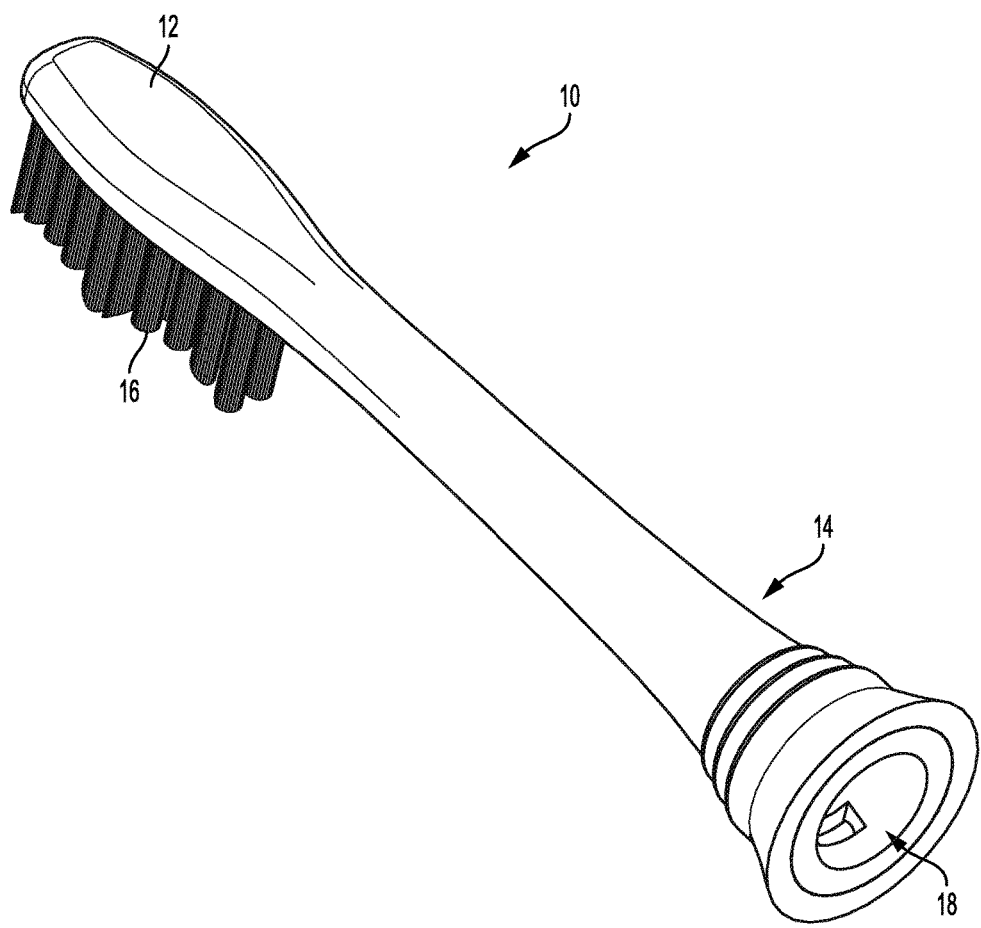
FIG. 1 is a perspective view of a toothbrush head with a coupling member therein according to one embodiment.

In one embodiment, a brush head 10 is couplable to a drive shaft of an electric toothbrush handle, as shown in FIG. 1. The brush head 10 includes a brush section 12 that has multiple bristles 16 attached thereon. The brush head 10 also has a stem 14, which extends from the brush section 12. The stem 14 has an opening therein (15 in FIG. 5) for receiving and mounting a coupling member 18. The attachment of the coupling member 18 to the stem 14 is further described in detail with reference to FIG. 2.

Figure 2:
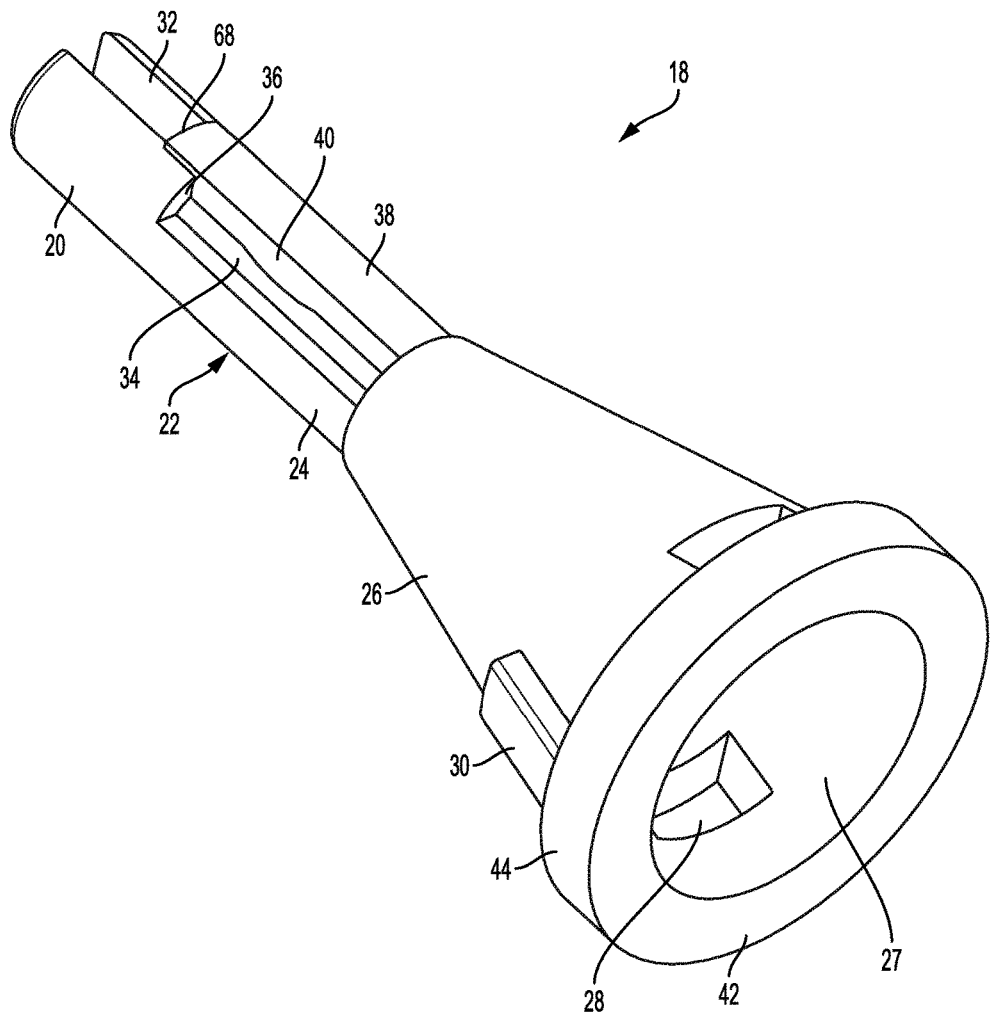
FIG. 2 is a perspective view of a coupling member of a toothbrush head according to the embodiment in FIG. 1.

As shown in FIG. 2, in the illustrated embodiment, the coupling member 18 has a body 26, which has an opening 27 for receiving a drive shaft of the electric toothbrush handle. The body 26 has one or more mounting holes 28 that are positioned to engage with one or more mounting ridges (54 in FIG. 5) of the stem so that the coupling member can be mounted to the stem. The coupling member 18 also has a handle coupling section 22, which has a wall 24 with an aperture 34 inside the wall. The wall 24 has at least two longitudinal slits 36 that form a resilient wall 38 in between. The resilient wall 38 is positioned to touch the drive shaft when the drive shaft is inserted into the aperture inside the wall 24 and exert a return force inward towards the drive shaft to achieve a tight coupling with the drive shaft.

In the illustrated embodiment, the cross-section of the coupling section 22 may corresponds to the size of the stem 14 of the brush head 10, for example, at about ⅛ inch in diameter measured from outside, with a length about ½ inch. The body 26 may extend from the coupling section and flares outward to the opening 27 to form a cone shape. The opening 27 may be of various sizes, for example, at ½ inch in diameter as measured from outside at its widest point.

Figure 5:
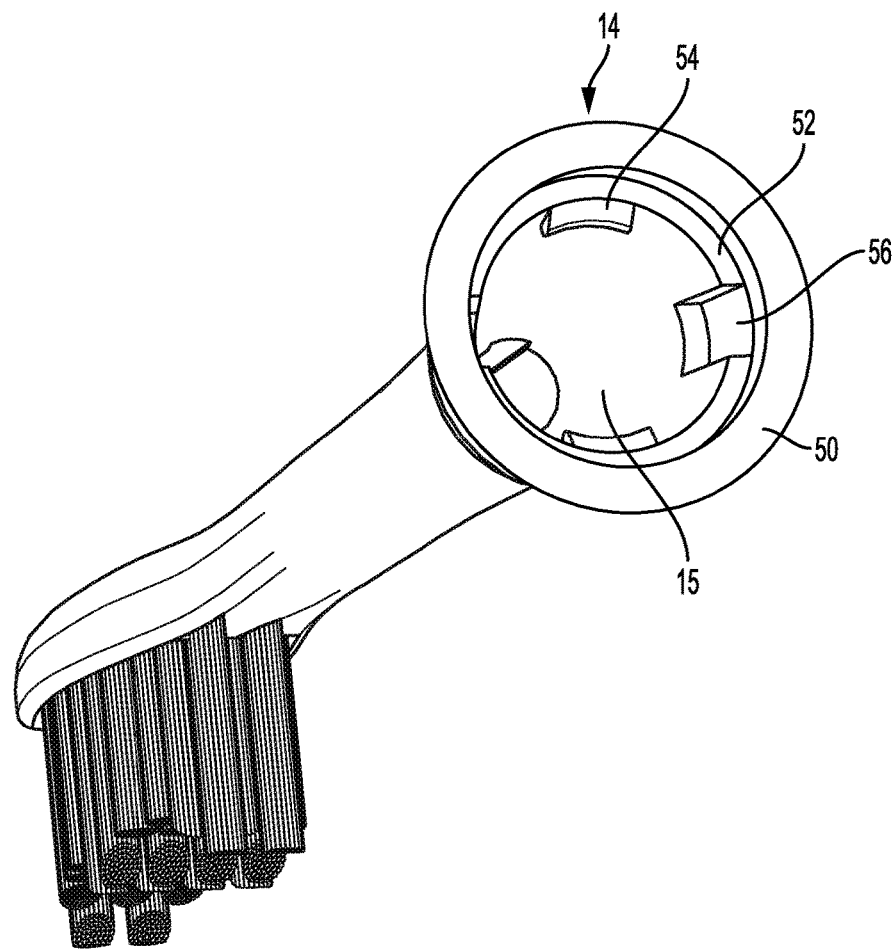
FIG. 5 is a bottom perspective view of the stem of the toothbrush head according to the embodiment in FIG. 1.

In various embodiments, multiple engagements between various parts may additionally facilitate the tight coupling between the brush head and the coupling member. For example, in FIG. 2, the coupling member 18 may have one or more mounting blocks 30 extending from outside the body 26 and that are positioned to engage with one or more mounting receptacles 56 (in FIG. 5) inside the opening 15 (FIG. 5) of the stem 14 (FIG. 5). This engagement between each mounting block 30 and its corresponding mounting receptacles 56 (in FIG. 5) will further lock the coupling member into position to prevent the coupling member from being pushed in or rotating about the axis of the stem.

Figure 3:
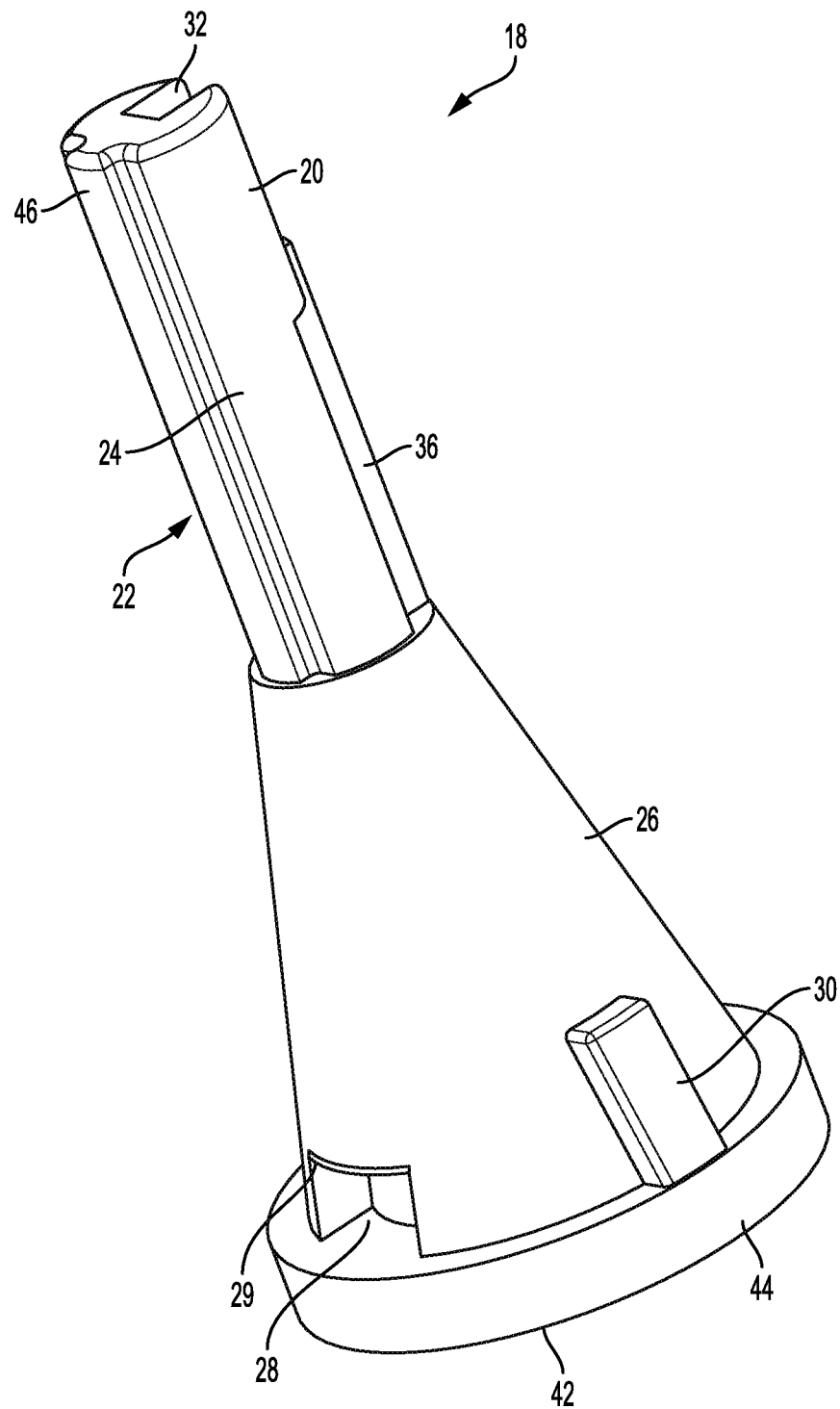
FIG. 3 is a side perspective view of the coupling member of the toothbrush head according to the embodiment in FIG. 1.
Figure 6:
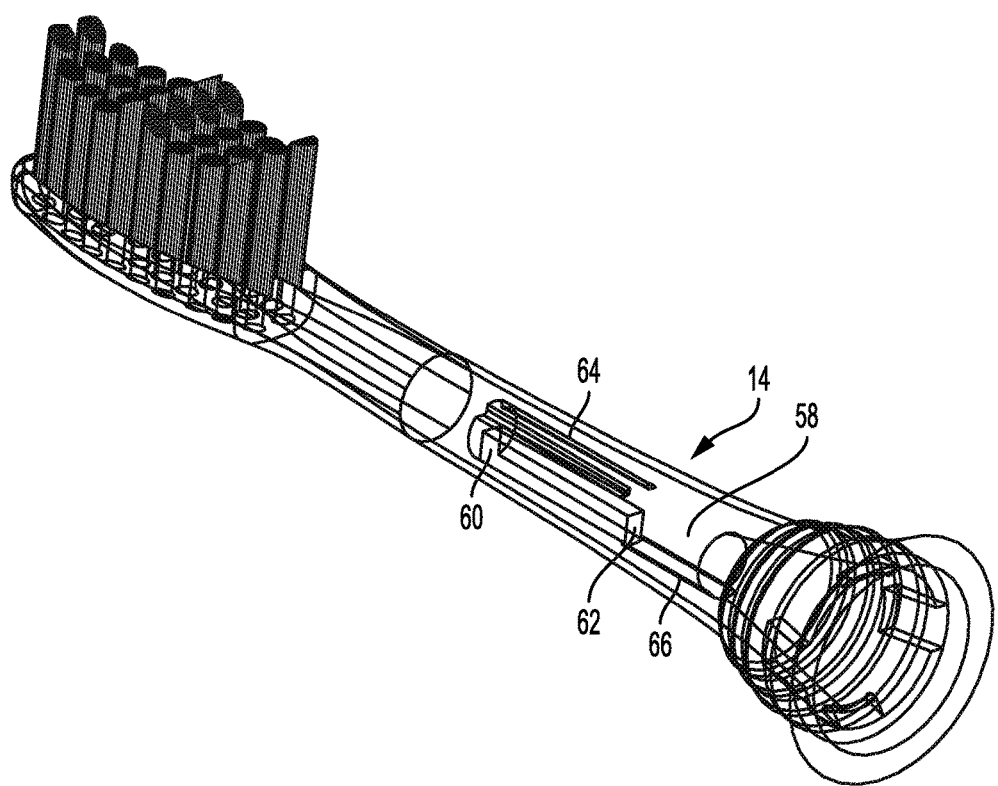
FIG. 6 is a wireframe of the stem of the toothbrush head according to the embodiment in FIG. 1.
Figure 7:
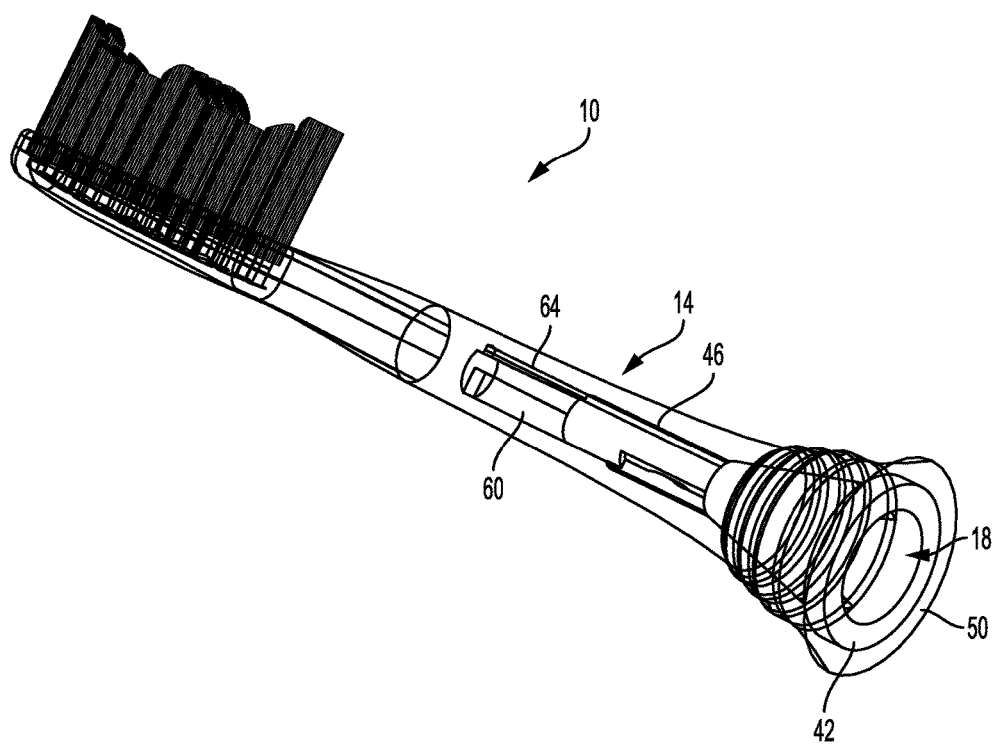
FIG. 7 is a transparent view of the toothbrush head with the stem therein according to the embodiment in FIG. 1.

Alternatively, and/or additionally, as shown in FIG. 3, the coupling member 18 may include a head section 20, which extends from the handle coupling section 22 and has a longitudinal ridge 46 on outside surface of the head section and the longitudinal ridge 46 is positioned to engage with a longitudinal channel inside the stem (shown in 64 in FIG. 6). This engagement between the longitudinal ridge 46 and the longitudinal channel 64 inside the stem prevents the coupling member from rotational movement about the axis of the stem. It further provides a guide to facilitate the insertion of the coupling member into the stem. Optionally, as shown in FIG. 3, the longitudinal ridge 46 may also extend longitudinally from the head section 20 along outside surface of the wall 24 of the handle coupling section 22 of the coupling member to further enhance the engagement between the coupling member 18 and the stem and prevent rotational movement or twisting of the coupling member relative to the stem.

Alternatively, and/or additionally, as shown in FIG. 3, the head section 20 may also have a grooved mounting channel 32, which is positioned to engage with a ridge block 60 (in FIG. 6) in the stem to further facilitate the coupling of the coupling member and the stem. Optionally, as shown in FIG. 6, the ridge block 60 inside the stem 14 may have a stopping edge 62, which is positioned to touch the end 68 of mounting channel 32 (in FIG. 2) of the coupling member to prevent the coupling member from further being inserted into inside the stem.

Alternatively, and/or additionally, as shown in FIGS. 2 and 5, the opening 15 of the stem 14 may have a base platform, and the opening 27 of the body 26 of the coupling member 18 may also have a base platform that is positioned to be flush with the base platform of the stem when the coupling member and the stem are fully engaged (as shown in FIG. 1).

Alternatively, and/or additionally, the coupling member 18 may have an engagement means for further coupling the brush head to the drive shaft of the toothbrush handle. This engagement means may include a raised portion 40 that extends inward from the resilient wall 38 and is positioned to touch the drive shaft when the drive shaft is inserted into the aperture 34 of the handle coupling section 22. The raised portion 40, when touching the drive shaft, will also raise the resilient wall 38 outward, thus to increase the inward returning force of the resilient wall 38, whereby a tighter coupling between the coupling member and the drive shaft of the electric toothbrush handle can be achieved.

Figure 4:
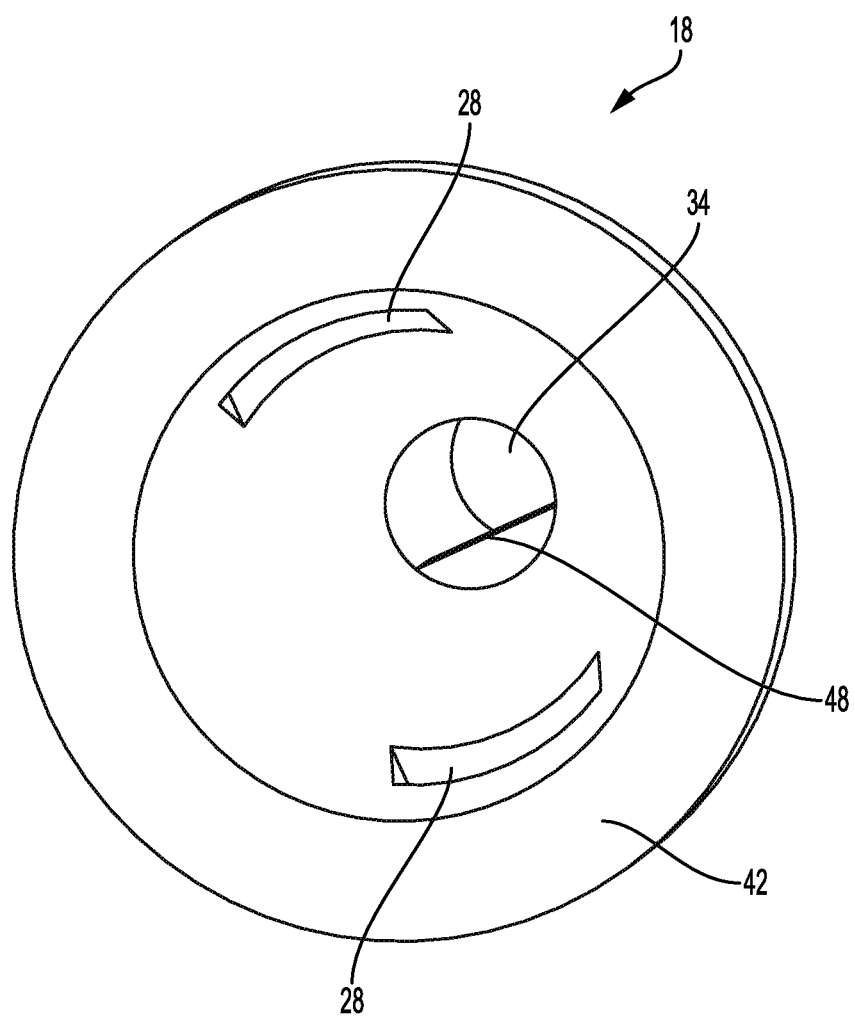
FIG. 4 is a bottom perspective view of the coupling member of the toothbrush head according to the embodiment in FIG. 1.

Alternatively, and/or additionally, as shown in FIG. 4, the handle coupling section may have a flat engaging surface 48 inside the aperture 34 and is positioned to mate with a flat surface of the drive shaft so that the handle coupling section and the drive shaft can be fully coupled.

Alternatively, and/or additionally, as shown in FIGS. 2 and 5, the stem 14 may have a sitting platform 52 along a portion or all of the inside perimeter of the opening 15, whereas the opening 27 of the body 26 of the coupling member 18 has a base ring 44 around a portion or all of the outside perimeter of the opening 27 which is positioned to mate with the sitting platform 52 of the stem. This mating arrangement will prevent the coupling member from further moving into the stem when it is fully coupled to the stem. This mating arrangement will also make it easier for base platform 42 of the coupling member 18 and the base platform 50 of the stem 14 to flush when they are being assembled together.

Alternatively, and/or additionally, as shown in FIG. 2, the resilient wall 38 the handle coupling section 22 may raise outward above outside surface of the rest of the wall, while the raised resilient wall 38 forms a longitudinal guide that is positioned to engage with a coupling channel 66 inside the stem 14 (in FIG. 6), to further facilitate the coupling of the coupling member and the stem. In one embodiment, as shown in FIG. 2, the raised resilient wall 38 extends from the end 68 of the mounting channel 32. Correspondingly, as shown in FIG. 6, the coupling channel 66 in the stem may extend from the stopping edge 62 of the ridge block 60 longitudinally outward towards the opening (15 in FIG. 5) to engage with the raised resilient wall 38 of the coupling member.

To enable locking of the coupling member to the stem, as shown in FIG. 3, the coupling member 18 may have a locking ridge 29 raising from outside surface of the body 26 proximate to an edge of the one or more mounting holes 28 and positioned to lock the one or more mounting ridges of the stem thereunto (54 in FIG. 5).

Alternatively, and/or additionally, as shown in FIGS. 2 and 5, at least a portion of the head section 20 and/or the handle coupling section 22 of the coupling member 18 are in a cylindrical shape. The body 26 of the coupling member 18 may be in a cone shape near the opening 27 and a portion of the stem proximate to the opening 15 may also have a cone shape that corresponds to the cone shape of the body 26 of the coupling member 18 so that the stem may receive the coupling member into its opening 15.

The various embodiments disclosed in this patent document provide advantages over the prior art, whether stand-alone or combined. For example, the resilient wall of the handle coupling section of the coupling member that is positioned to engage with the drive shaft of the electric toothbrush handle may be made from the same wall of the handle coupling section of the coupling member, which requires no metal spring or other separate resilient member. This both achieves a tight coupling (because there is no separate part) and reduces the cost of making. Further, multiple engagements of various parts of the stem and the coupling member all facilitate a tight coupling between the coupling member and the stem, and thus improve the stability of the brush head as it is operating under the high speed vibrations of the motor inside the handle.

Further, the toothbrush head may be easy to manufacture as all the parts can be made of plastic or polyester materials. The cone shaped opening of the stem may facilitate easy receiving and coupling of the coupling member into the stem, and multiple engagement means, such as, the longitudinal ridge of the coupling member and the corresponding longitudinal channel in the stem, the mounting channel of the coupling member and the corresponding ridge block in the stem, the raised resilient wall of the coupling member and the corresponding coupling channel in the stem, the mounting block of the coupling member and the corresponding mounting channel in the stem, the base ring of the coupling member and the mating sitting platform in the stem, the mounting holes of the coupling member and the mounting ridges in the stem, each may facilitate easy sliding and positioning of the coupling member into the stem and secure mounting of the coupling member to the stem.

Other advantages of the present invention can be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as defined in the claims.

The invention claimed is:

1. A toothbrush head comprising:
   a brush section having a plurality of bristles attached thereon;
   a stem extending from the brush section, wherein the stem defines an opening therein and comprises one or more mounting ridges on inside wall of the opening; and
   a coupling member mountable to inside the opening of the stem, wherein the coupling member comprises:
     a body having an opening configured to receive a drive shaft of an electric toothbrush handle into the coupling member, and one or more mounting holes that are positioned to engage with the one or more mounting ridges of the stem to secure the coupling member to the stem in position, and
     a handle coupling section extending from the body and having a wall and defining an aperture within the wall for receiving the drive shaft, wherein the wall has at least two longitudinal slits and a resilient wall between the two slits, further wherein the resilient wall is positioned to engage with the drive shaft when the drive shaft is inserted into the coupling member.

2. The toothbrush head of claim 1, wherein:
   the stem further comprises a ridge block and a longitudinal channel on the inside wall of the opening; and
   the coupling member further comprises a head section extending from the handle coupling section, wherein the head section has a longitudinal ridge that is positioned to engage with the longitudinal channel of the stem, wherein the head section also defines a mounting channel that is positioned to engage with the ridge block of the stem.

3. The toothbrush head of claim 2, wherein an end of the mounting channel is positioned to touch a stopping edge of the ridge block so that the coupling member is prevented from further moving into the stem.

4. The toothbrush head of claim 2, wherein the longitudinal ridge also extends longitudinally along an outside wall of the handle coupling section of the coupling member.

5. The toothbrush head of claim 3, wherein:
   the stem further comprises a coupling channel on an inside surface; and
   the resilient wall of the handle coupling section raises outward from the handle coupling section and forms a guide that is positioned to engage with the coupling channel of the stem.

6. The toothbrush head of claim 5, wherein the coupling channel of the stem extends from the stopping edge of the ridge block of the stem to the opening of the stem.

7. The toothbrush head of claim 2, wherein at least a portion of the head section and a portion of the handle coupling section of the coupling member are in a cylindrical shape.

8. The toothbrush head of claim 7, wherein at least a portion of the body of the coupling member is in a cone shape and a portion of the stem proximate to the opening also has a cone shape that corresponds to the cone shape of the body of the coupling member.

9. The toothbrush head of claim 1, wherein:
   the opening of the stem has a base platform; and
   the opening of the body of the coupling member has a base platform that is positioned to be flush with the base platform of the stem.

10. The toothbrush head of claim 1, wherein the resilient wall of the handle coupling section has a raised portion extending inward and positioned to touch the drive shaft so that the drive shaft is tightly coupled to the handle coupling section while received in the aperture of the handle coupling section.

11. The toothbrush head of claim 1, wherein the handle coupling section defines a flat engaging surface inside the aperture that is positioned to mate with a flat surface of the drive shaft.

12. The toothbrush head of claim 1, wherein:
   the stem defines a mounting receptacle inside the opening of the stem; and
   the body of the coupling member has a mounting block extending from an outside surface of the body and positioned to engage with the mounting receptacle of the stem.

13. The toothbrush head of claim 1, wherein:
   the stem defines a sitting platform along at least a portion of an inside perimeter of the opening of the stem; and
   the body of the coupling member has a base ring around at least a portion of an outside perimeter of the opening of the body and positioned to mate with the sitting platform of the stem.

14. The toothbrush head of claim 1, wherein the body of the coupling member has a locking ridge raising from an outside surface of the body proximate to an edge of the one or more mounting holes and positioned to lock the one or more mounting ridges of the stem thereunto.

15. A toothbrush head comprising:
   a brush section having a plurality of bristles attached thereon;
   a stem extending from the brush section, wherein the stem defines an opening therein and comprises one or more mounting ridges on inside wall of the opening, further wherein the opening has a base platform; and
   a coupling member mountable to inside the opening of the stem, wherein the coupling member comprises:
     a body having an opening configured to receive a drive shaft of an electric toothbrush handle into the coupling member, one or more mounting holes that are positioned to engage with the one or more mounting ridges of the stem to secure the coupling member to the stem in position, and one or more locking ridges each raising from an outside surface of the body proximate to an edge of the one or more mounting holes and positioned to lock the one or more mounting ridges of the stem thereunto, wherein the opening of the body has a base platform that is positioned to be flush with the base platform of the stem, and
     a handle coupling section extending from the body and having a wall and defining an aperture within the wall for receiving the drive shaft, wherein the wall has at least two longitudinal slits and a resilient wall between the two slits, further wherein the resilient wall is positioned to engage with the drive shaft when the drive shaft is inserted into the coupling member.

16. The toothbrush head of claim 15, wherein:
the stem further comprises a ridge block and a longitudinal channel on the inside wall of the opening; and
the coupling member further comprises a head section extending from the handle coupling section, wherein the head section has a longitudinal ridge that is positioned to engage with the longitudinal channel of the stem, wherein the head section also defines a mounting channel that is positioned to engage with the ridge block of the stem.

17. The toothbrush head of claim 15, wherein the resilient wall of the handle coupling section has a raised portion extending inward and positioned to touch the drive shaft so that the drive shaft is tightly coupled to the handle coupling section while received in the aperture of the handle coupling section.

18. The toothbrush head of claim 15, wherein:
the stem defines a mounting receptacle inside the opening of the stem; and
the body of the coupling member has a mounting block extending from the outside surface of the body and positioned to engage with the mounting receptacle of the stem.

19. The toothbrush head of claim 15, wherein:
the stem defines a sitting platform along at least a portion of an inside perimeter of the opening of the stem; and
the body of the coupling member has a base ring around at least a portion of an outside perimeter of the opening of the body and positioned to mate with the sitting platform of the stem.

20. The toothbrush head of claim 15, wherein:
the stem further comprises a coupling channel on an inside surface; and
the resilient wall of the handle coupling section raises outward from the handle coupling section and forms a guide that is positioned to engage with the coupling channel of the stem.

* * * * *